(12) United States Patent
Ishiguro et al.

(10) Patent No.: US 6,330,059 B1
(45) Date of Patent: Dec. 11, 2001

(54) OPTICAL SYSTEM FOR DETECTING SURFACE DEFECTS, A DISK TESTER AND A DISK TESTING METHOD

(75) Inventors: Takayuki Ishiguro; Hiroshi Nakajima, both of Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/696,047

(22) Filed: Oct. 26, 2000

(30) Foreign Application Priority Data

Oct. 27, 1999 (JP) .................................................. 11-305647

(51) Int. Cl.⁷ .................................................. G01N 21/88
(52) U.S. Cl. ...................... 356/237.5; 356/237.2
(58) Field of Search .............. 356/237.1–237.5, 356/445

(56) References Cited

U.S. PATENT DOCUMENTS 5,875,027   2/1999  Ishiguro et al. .................. 356/243.4
6,271,916 * 8/2001  Marxer et al. ..................... 356/237.3

FOREIGN PATENT DOCUMENTS 10-325713   12/1998  (JP) .

* cited by examiner

*Primary Examiner*—Frank G. Font
*Assistant Examiner*—Michael P. Stafira
(74) *Attorney, Agent, or Firm*—Mattingly, Stanger & Malur, P.C.

(57) ABSTRACT

Annular rays of light are received by a hollow optical member and focused as light beams on the surface of a disk to be tested and as the scattered light from the disk surface travels toward the hollow portion of the optical member, it is received by an objective lens and then received by a light receiver via the objective lens.

14 Claims, 4 Drawing Sheets

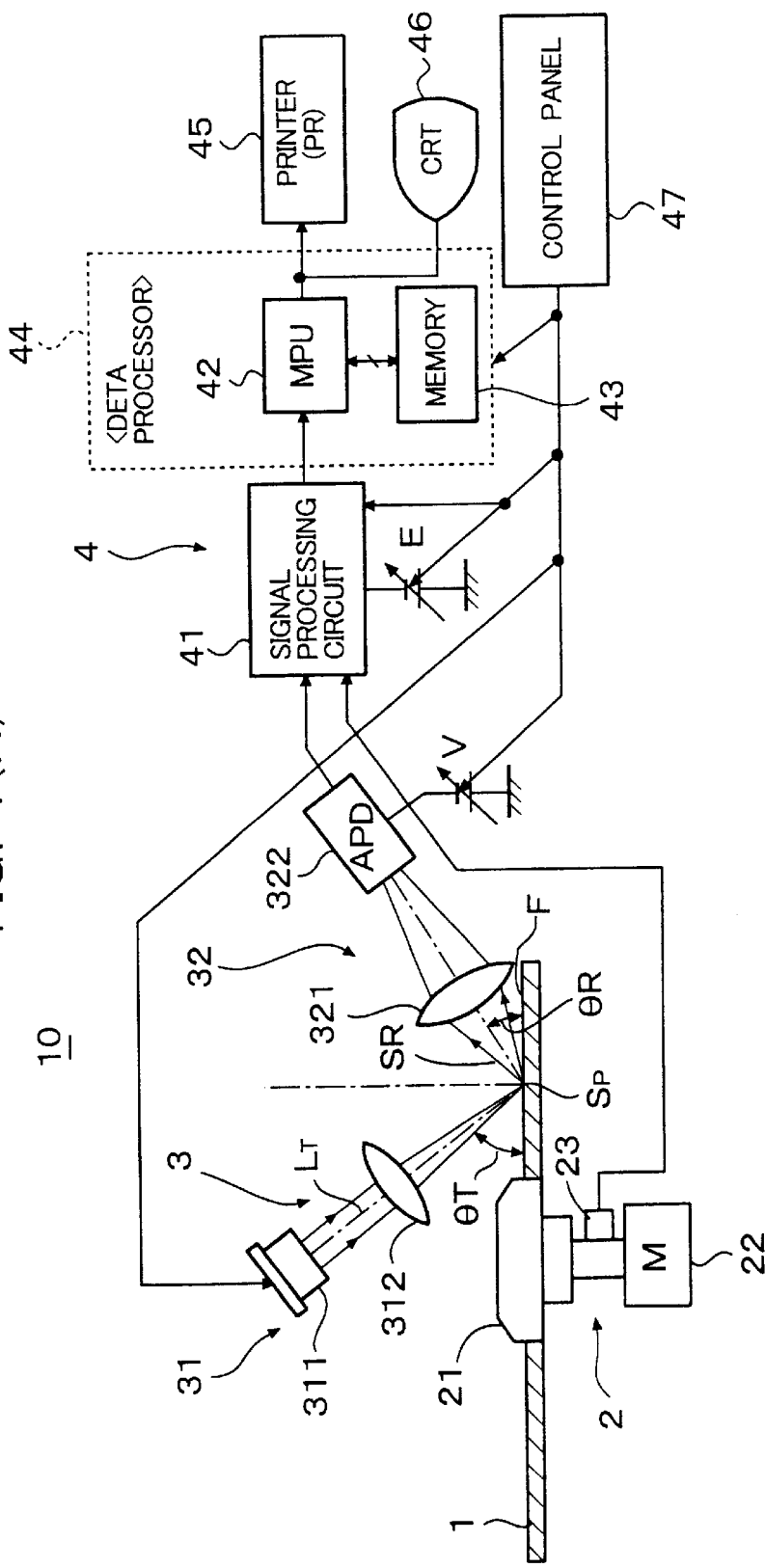
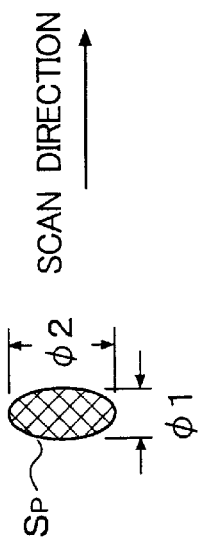
FIG. 4(A)
FIG. 4(B)
SCAN DIRECTION

OPTICAL SYSTEM FOR DETECTING SURFACE DEFECTS, A DISK TESTER AND A DISK TESTING METHOD

TECHNICAL FIELD

This invention relates to an optical system for detecting surface defects, a disk tester and a disk testing method. More particularly, the invention relates to an optical system for use in a detector of surface defects on magnetic disks or glass substrates therefor by which the size of scratches, nicks, burs and other defects on the glass surface can be defected either alone or in combination with their depth or height or other dimensions and in high precision that is hardly affected by the defects on the reverse surface of the substrate. The invention also relates to a disk tester and a disk testing method that tests disk for any surface defects using this optical system.

BACKGROUND ART

Hard magnetic disks to be used as recording media in a computer system are tested for any surface defects and their size during fabrication at the stage of either a substrate or a finished disk having a magnetic coating (for the sake of convenience, both types are hereunder collectively referred to as "magnetic disks" or more simply as "disks").

Most of the disks in current use are 3.3 inches or less in diameter and their recording density has been increasing dramatically due to the use of GMR heads. These disks formerly used aluminum substrates but they now use glass disks having smaller heat expansion ratios and thicknesses in the order of 0.6–0.8 mm.

FIG. 4A shows the layout of the essential part of a conventional disk tester, or an apparatus for detecting surface defects on magnetic disks which is generally indicated by 10. The apparatus 10 consists of three major components, a rotating mechanism 2, a detecting optical system 3 and a surface defect detecting and processing unit 4. A disk 1 to be tested is mounted on a spindle 21 in the rotating mechanism 2 and driven to rotate with a motor (M) 22. The detecting optical system 3 has projection optics 31 comprising a laser light source 311 and a focusing lens 312. The laser beams $L_T$ from the light source 311 are focused by the lens 312 to form a spot $S_P$ that illuminates the surface of the disk 1.

If the disk 1 moves in the direction of X axis, the spot $S_P$ moves in the direction of the radius R of the disk 1 so that its surface is scanned spirally. In order to minimize the scan time, the spot $S_P$ takes on an elliptical shape having a minor axis $\phi_1$ and a major axis $\phi_2$ (see FIG. 4B). The major axis $\phi_2$ is set perpendicular to the scanning direction so as to increase the scan width.

A defect F on the surface of the disk 1 scatters the light of spot $S_P$. The scattered light $S_R$ is condensed by a condenser lens 321 in light receiving optics 32 and received by a light receiver 322 which is composed of photoelectric transducers such as avalanche photodiodes (APD) or photomultiplier tubes (PMT). An output signal from the light receiver 322 is input to a signal processing circuit 41 in the surface defect detecting and processing unit 4. The defect F is detected by the signal processing circuit 41 and its size is classified or calculated from the amplitude of said output signal. Being a circuit for detecting defects by a sampling technique, the signal processing circuit 41 comprises the following basic components: an amplifier for amplifying the output signal from the light receiver 322; a sampling circuit for detecting a peak defect value which, in response to pulses from a rotary encoder 23, samples peak values for those amplified output signals which represent defects that exceed noise; an A/D converter for digitizing the sampled peak values; and a position data generating circuit which generates data about position on the disk in response to pulses from the rotary encoder 23.

The data about the size of each defect and the data about its position on the disk are subjected to A/D conversion within the signal processing circuit 41 and thence input to a data processor 44 comprising an MPU 42, a memory 43, etc. In the data processor 44, the number of defects is counted for each size and the result is printed out by a printer (PR) 45 together with the position of each defect on the disk. Alternatively, the size of each defect is shown on the screen of a CRT 46 or other display together with its position on the disk. The count of defects of each size is also displayed as a separate piece of data.

The rotary encoder 23 is provided either adjacent to or in engagement with the rotating shaft of the motor 22. It detects the reference position for disk rotation and the amount of its rotation and sends the associated pulse signals to the signal processing circuit 41.

Defects F on the disk 1 can assume various shapes as exemplified in FIG. 5. Defect $F_h$ resembles a saucer having a diameter $D_h$ much greater than depth $d_h$. Defect $F_P$ resembles awell having a diameter $D_P$ much smaller than depth $d_P$ and is commonly called a "pit". Both types of defects frequently occur as isolated phenomena. In contrast, $F_s$ is a linear defect called a "scratch" and its section can have various values of width $w_s$ and depth $d_s$. Needless to say, the disk can have surface defects F of other shapes.

Aside from these defects in the form of a recess, burs or protrusions such as "extraneous substances" that typically result from the deposition of fine particles can occur in various sizes and heights.

In order to achieve satisfactory detection of defects of various shapes and sizes, the disk tester 10 provides optimum settings of detection sensitivity-related factors via a control panel 47 which include the angle of projection $\theta_T$ of laser beams $L_T$ from the projection optics 31, the angle of light reception $\theta_R$ by the light receiving optics 32, the voltage V to be applied to the light receiver 322 (APD), the gain of the built-in amplifier in the signal processing circuit 41, the threshold voltage E for noise rejection, and the laser output from the laser light source 311. To perform sensitivity adjustment, either an actual disk having sample defects (e.g. saucers, pits or scratches) of known sizes or an actual disk having burs of specified heights are used as a sample.

An invention based on this concept has been applied for patent by the Assignee under Unexamined Published Japanese Patent Application No. 325713/1998 entitled "Method and apparatus for detecting surface defects". According to this invention, testing for defects is performed using a sensitivity calibration disk having simulated defect rows of progressively varying sizes for high or low spots of irregularities and those simulated defect rows which progressively increase or decrease in size are radially displayed as the result of testing and the detection sensitivity is adjusted in accordance with the displayed test result.

The Assignee filed a United States patent application on a sensitivity calibration disk to be used by the detecting apparatus and U.S. Pat. No. 5,875,027 has issued, teaching the technology illustrated in the aforementioned FIGS. 4 and 5.

However, even such detection method or apparatus does not work satisfactorily if the disk to be tested is a glass disk having a thickness of about 0.6–0.8 mm. In response to vertical displacements of the disk, the light of laser beams $L_T$ scattered by the defects on the reverse surface of the disk or the extraneous substances deposited on it travels back to the obverse surface or the reflected light from the reverse surface becomes noise and, as a result, not only the precision in detection of scratches, nicks and burs on the glass surface is lowered but also the defects on the reverse surface of the disk are erroneously recognized as defects on the obverse surface.

SUMMARY OF THE INVENTION

The present invention has been accomplished under these circumstances and has as an object providing an optical system by which surface defects on disks can be detected with high precision that is hardly affected by the defects on their reverse surface.

Another object of the invention is to provide a disk tester by which surface defects on disks can be detected with high precision that is hardly affected by the defects on their reverse surface.

A further object of the invention is to provide a method that can be applied to operate this disk tester.

The first and second objects of the invention can be attained by an optical system for detecting surface defects and a disk tester, each comprising a light source for generating annular rays of light, a hollow optical member that has a ring-shaped surface for receiving the annular rays of light and which focuses the received annular rays of light as light beams on the surface of a disk to be tested, an objective lens that is provided within the hollow portion of the optical member to receive scattered light, and an imaging lens that receives the light from the objective lens and forms the image of scan position on a light receiver.

The third object of the invention can be attained by a disk testing method which comprises the steps of receiving annular rays of light by a hollow optical member, focusing the received annular rays of light as light beams on the surface of a disk to be tested, receiving the scattered light from the disk surface by an objective lens as it travels toward the hollow portion of the optical member, and receiving the scattered light by a light receiver via the objective lens.

According to another aspect of the invention, the angle of illumination with the annular rays of light is set at such a value that the point at which they are focused by the optical member will hardly reach the reverse surface of the disk in spite of its vertical displacements.

Thus, the use of an optical member that focuses the annular rays of light as light beams on the surface of a disk to be tested permits the illuminating light to be focused on the disk surface toward the test point from the surrounding area. As a result, the illuminating light diffuses in areas backward of the point of focus and there is only a small likelihood for the generation of intense, inwardly travelling scattered light.

In addition, the scattered light from the disk surface on which the light beams have been focused is received by the objective lens fitted in the hollow portion of the optical member, so the objective lens receives little of the highly directional scattered light from the defects and extraneous substances on the reverse surface of the disk, as well as the reflected light from that reverse surface. This contributes to a higher S/N ratio of the signals detected by the light receiver.

A further improvement in S/N ratio can be realized by setting the angle of illumination of the annular rays of light at such a value that the point at which they are focused will hardly reach the reverse surface of the disk to be tested in spite of its vertical displacements.

As a result, one can easily produce an optical system for detecting surface defects and a disk tester by which surface defects on disks can be detected with high precision that is hardly affected by the defects on the reverse surface of the disk and which provide particular ease in detecting the size of scratches, nicks, burs and other defects on the glass surface, preferably together with their depth or height.

BRIEF DESCRIPTION OF THE DRAWINGS

FIG. 4 illustrates the layout of the essential components of a conventional magnetic disk tester.

DESCRIPTION OF THE PREFERRED EMBODIMENT

Figure 1:
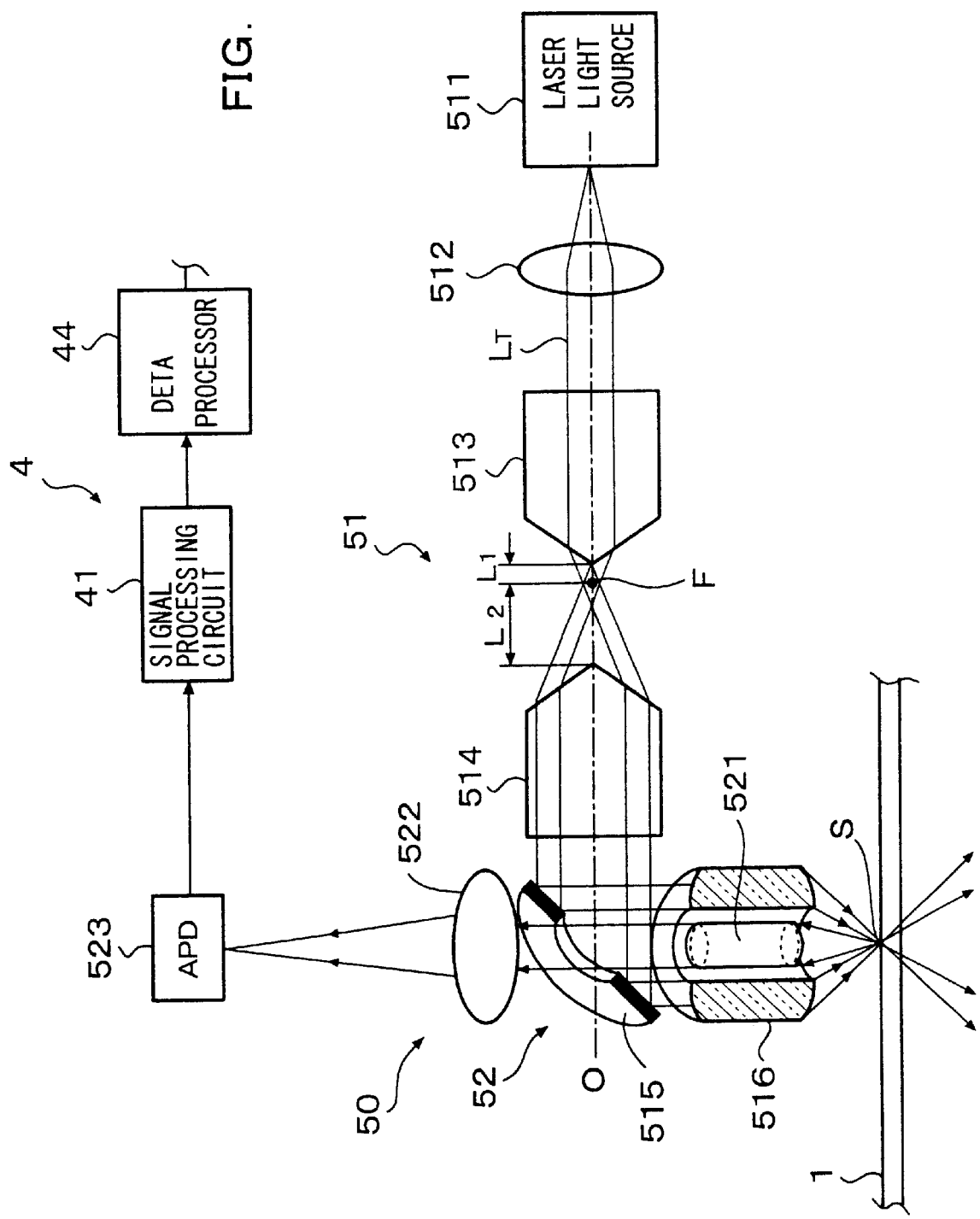
FIG. 1 is a block diagram for an example of an optical system for detecting surface defects by applying the concept of the invention.

Generally indicated by 50 in FIG. 1 is an optical system for detecting surface defects that is used in a disk tester. Generally indicated by 51 is projection optics which comprise a laser light source 511 comprising laser diodes (LD), a collimator lens 512, a first conical lens 513 pointed at the front end and a second conical lens 514 pointed at the rear end. The laser beams $L_T$ from the light source 511 pass through the collimator lens 512 to become parallel light having a circular cross section which is launched into the first conical lens 513 through the rear end so that it is focused at point F on the optical axis O. Light beams radiating from the point of focus F are launched as annular light into the second conical lens 514, whereupon annular light beams are generated from its front face which is perpendicular to the optical axis O. In the embodiment under consideration, $L_1$ or the distance between the point of focus F and the first conical lens 513 is set to be smaller than $L_2$ or the distance between the point F and the second conical lens 514. The angles of inclination of the cones of the two conical lenses are substantially the same.

The annular light emerging from the second conical lens 514 illuminates the circumferential reflective surface of a circular doughnut-shaped mirror 515 inserted into the optical path of light receiving optics 52 at an angle of about 45 degrees. The light is bent down by this mirror to illuminate the top surface of a hollow cylindrical objective lens 516 having a magnifying power comparable to that of a microscope. The annular light beams passing through this objective lens are focused at the test point S on a disk 1. The magnifying power of the objective lens 516 is in the range between about 20x and 50x and located about 5–10 mm above the surface of the disk 1. The angle of illumination with the annular light beams from the objective lens 516 ranges between $\theta_1$ and $\theta_2$ (see FIG. 2) and is typically no more than 70 degrees, preferably no more than 65 degrees, in terms of the angle of elevation above the disk surface.

With this arrangement of optical elements, even if the disk 1 is a glass disk as thin as about 0.6–0.8 mm which is rotating to experience vertical displacements of the surface, substantially all rays of illuminating light are prevented from being focused on the reverse surface of the disk and the reception of scattered light from the defects and extraneous substances on that reverse surface is suppressed or entirely inhibited.

In this case, the illuminating light travelling toward the test point from the surrounding area at angles within the range between $\theta_1$ and $\theta_2$ diffuses in areas backward of the point of focus and there is only a small likelihood for the occurrence of intense, inwardly travelling scattered light.

The light receiving optics 52 also include a light receiving objective lens 521 having a magnifying power comparable to that of the cylindrical objective lens 516 (i.e., ca 20×–50×) and this is fitted within the hollow portion of the objective lens 516, with the front end positioned inwardly of the latter. Since the objective lens 521 is located within the cylindrical objective lens 516, it is less likely to receive the scattered light from the defects and extraneous substances on the reverse surface of the disk.

The scattered light from the test point S on the disk 1 which has been received by the objective lens 521 is parallel light that passes through the center hole in the mirror 515 to be launched into an imaging lens 522 which in turn forms the image of the test point S on the light receiving surface of an APD sensor 523. The APD sensor 523 corresponds to the light receiver 322 in FIG. 4. A detection signal (output signal) from the APD sensor 523 is input to a signal processing circuit 41 in a surface defect detecting and processing unit 4, where the defect F is detected. The size of the defect is classified or calculated from the amplitude of the output signal. The sensitivity of the signal processing circuit 41 is adjusted in accordance with the settings of various types of defects that have been predetermined by the circuit which then detects the size of the defect, optionally together with its depth or height.

Figure 2:
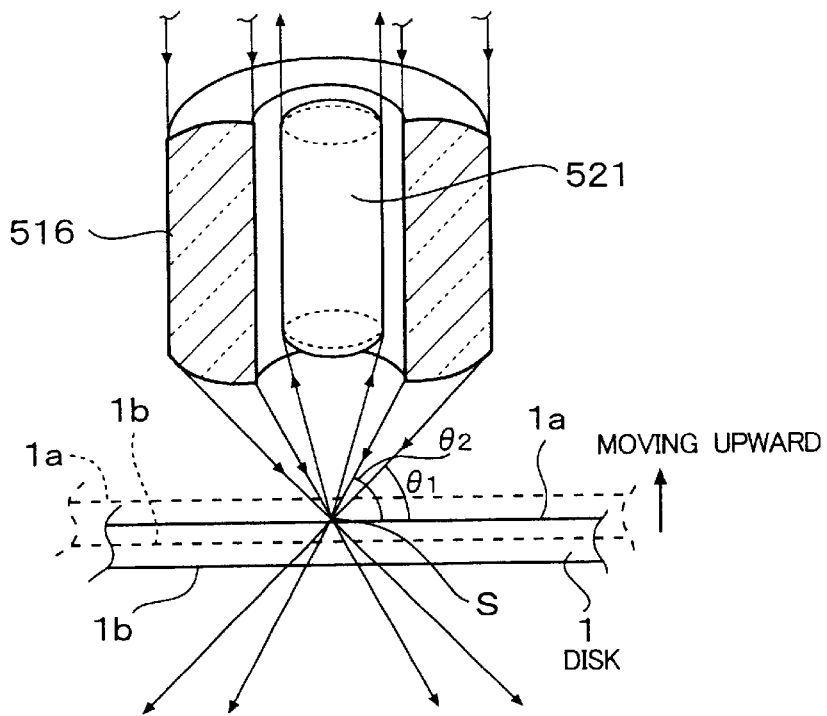
FIG. 2 illustrates the relationship between the illuminating light incident on a disk surface and the scattered light from a defect on that surface.

FIG. 2 shows enlarged the relationship between the illuminating light from the cylindrical objective lens 516 and the scattered light to the objective lens 521. As shown, the angle of illumination from the cylindrical objective lens 516 ranges between $\theta_1$ and $\theta_2$ relative to the surface 1a of the disk 1. The annular light is focused at the test spot S with the angle of illumination between $\theta_1$ and $\theta_2$ being nearly equal to or smaller than about 65 degrees, so even if the point of focus of the illuminating light moves from the disk surface 1a into the bulk on account of vertical displacements of the disk 1, the diffusion of the incident light increases and its intensity decreases as the distance from the surface 1a increases toward the reverse surface 1b. As a result, less light is reflected from the reverse surface 1b and due to the diffusion of light from the test point S, only a very small amount of light is scattered from a defect on the reverse surface 1b to travel above the test spot S toward the objective lens 521 surrounded by the annular rays of light whereas a comparatively large amount of scattered light from defects near to the surface layer of the disk is selected by the objective lens 521. Even if the rotation of the disk 1 causes the positions of the disk surface 1a and the reverse surface 1b to change as indicated by the dashed lines, the point of focus S on the surface 1a is less likely to reach the reverse surface 1b and, hence, the detecting light is less susceptible to the effects of the defects and extraneous substances on the reverse surface 1b.

As a consequence, the S/N ratio of the detection signals obtained from the APD sensor 523 improves to realize the production of an optical system capable of precise detection of defects on the obverse surface of a disk without being adversely affected by the defects on its reverse surface.

Figure 3:
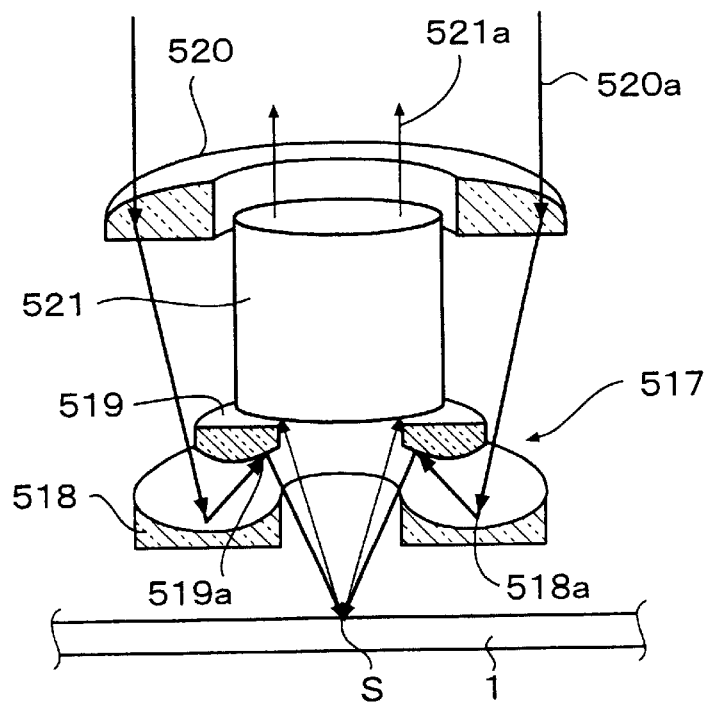
FIG. 3 shows in partial section an optical member for focusing annular light beams at the test point that consists of an annular lens and a focusing spherical mirror capable of multiple reflections.
Figure 5:
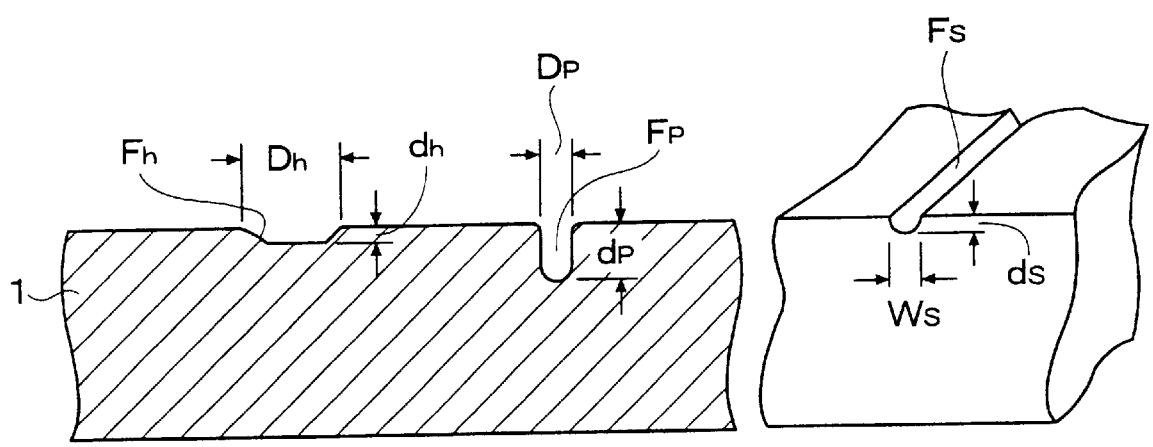
FIG. 5 illustrates the shapes of various defects on a disk.

FIG. 3 shows in partial section an optical member that may be substituted for the cylindrical objective lens 516 to focus the illuminating light at the test spot S on the disk 1 and which consists of an annular lens and a focusing spherical mirror capable of multiple reflections. The focusing spherical mirror 517 consists of a concave lower mirror 518 and a convex upper mirror 519. The two mirrors are doughnut-shaped and their principal parts overlap each other, with their inner reflective faces being opposed. The annular lens 520 which is provided above the spherical mirror 517 is fabricated by boring the center of a planoconcave lens to ensure an optical path 521a for the light to be received by the objective lens 521. According to another function of the annular lens 520, the annular rays of parallel light 520a falling down from the annular mirror 515 are refracted toward the test point S (the point of focus) so that they are guided to the concave lower mirror 518. The concave lower mirror 518 has a reflecting part 518a that does not overlap the convex upper mirror 519 but protrudes outward. This part receives the incident light (annular light 520a) from above and reflects it toward the convex upper mirror 519. The convex upper mirror 519 has an inner reflecting part 519a that guides the annular light 520a to be focused at the test point S. The combination of the two mirrors 518 and 519 thus enables the annular light to be focused at the test point S.

According to the configuration shown in FIG. 3, the annular light emerging from the second conical lens 514 in the projection optics 51 is bent down by the reflecting surface of the annular mirror 515 to illuminate a circular area in the light receiving part 518a of the concave lower mirror 518 and undergoes multiple reflections between the overlapping principal parts of the concave lower mirror 518 and the convex upper mirror 519. The reflected light is guided to the reflecting part 519a of the convex upper mirror 519 and, as in the case of the cylindrical objective lens 516, the annular rays of light defined by the width of the reflecting part 519a are focused to illuminate the test point S on the disk 1.

Again, the angle of illumination with the annular light is typically no more than 70 degrees, preferably nearly equal to or smaller than 65 degrees, in terms of the angle of elevation above the disk surface 1a.

In the preferred embodiment described above, the objective lens 521 as a light receiving optic that is provided within the cylindrical objective lens 516 as a projection optic has a magnifying power of about 20×–50×which corresponds to the magnifying power of the objective lens 516. However, this is not the sole case of the invention and the objective lens 521 may have a smaller magnifying power than the outer objective lens 516, provided that the former is located further backward of the latter with respect to the disk 1.

In the preferred embodiment, the disk surface to be tested is illuminated with annular rays of laser light which is preferably S-polarized laser beams. Of course, this is not the sole case of the invention and the disk surface may be illuminated with white light.

What is claimed is:

1. An optical system for detecting surface defects in which the surface of a disk to be tested is scanned with light beams and the resulting scattered light from said surface is received by a light receiver which then generates signals for defect detection, which comprises a light source for generating annular rays of light, a hollow optical member that has a ring-shaped surface for receiving said annular rays of light and which focuses the received annular rays of light as said light beams on said surface, an objective lens that is provided within the hollow portion of said optical member to receive said scattered light, and an imaging lens that receives the light from said objective lens and forms the image of scan position on said light receiver.

2. The optical system according to claim 1, wherein the angle of illumination of said surface with said annular rays of light by means of said optical member is set at such a value that the point at which said annular rays of light are focused by said optical member will hardly reach the reverse surface of said disk in spite of its vertical displacements.

3. The optical system according to claim 2, which further includes an annular mirror that receives said annular rays of light from said light source by means of the circumferential reflecting face outside the opening in said mirror and wherein said optical member uses said light receiving surface to receive the annular rays of light as reflected from said circumferential reflecting surface.

4. The optical system according to claim 3, wherein said light source comprises a laser light source, a collimator lens that receives the light from said laser light source and converts it to parallel light, a first conical lens that receives the parallel light from said collimator lens and focuses it at a specified point, and a second conical lens that receives the light from said specified point of focus at the rear end and which generates annular parallel light as said annular rays of light.

5. The optical system according to claim 4, wherein said optical member is a hollow cylindrical objective lens that uses one of the two circumferential areas to receive the annular rays of light as reflected from said circumferential reflecting surface and which allows the light emerging from the other circumferential area to be focused on said surface.

6. The optical system according to claim 5, wherein the angle of illumination with rays of light by means of said optical member is no more than 70 degrees in terms of the angle of elevation above said surface and both the magnifying power of said optical member and that of said objective lens are within the range of 20×–50×.

7. The optical system according to claim 4, wherein said optical member comprises an annular lens for receiving the annular rays of light as reflected from said circumferential reflecting surface and a doughnut-shaped focusing spherical mirror that receives the annular rays of light emerging from said annular lens and which subjects the received annular rays of light to multiple reflections so that the resulting light is focused on said surface.

8. The optical system according to claim 7, wherein the angle of illumination with said annular rays of light is no more than 70 degrees in terms of the angle of elevation above said surface and both the magnifying power of said optical member and that of said objective lens are within the range of 20×–50×.

9. A disk tester in which the surface of a disk to be tested is scanned with light beams and the resulting scattered light from said surface is received by a light receiver and which detects surface defects on the basis of output signals from said light receiver, which comprises a light source for generating annular rays of light, a hollow optical member that has a ring-shaped surface for receiving said annular rays of light and which focuses the received annular rays of light as said light beams on said surface, an objective lens that is provided within the hollow portion of said optical member to receive said scattered light, and an imaging lens that receives the light from said objective lens and forms the image of scan position on said light receiver, wherein the angle of illumination of said surface with said annular rays of light by means of said optical member is set at such a value that the point at which said annular rays of light are focused by said optical member will hardly reach the reverse surface of said disk in spite of its vertical displacements.

10. The disk tester according to claim 9, wherein said light source comprises a laser light source, a collimator lens that receives the light from said laser light source and converts it to parallel light, a first conical lens that receives the parallel light from said collimator lens and focuses it at a specified point, and a second conical lens that receives the light from said specified point of focus at the rear end and which generates annular parallel light as said annular rays of light, and which further includes an annular mirror that receives said annular rays of light from said light source by means of the circumferential reflecting face outside the opening in said mirror, said optical member using said light receiving surface to receive the annular rays of light as reflected from said circumferential reflecting surface.

11. The disk tester according to claim 10, wherein said optical member is a hollow cylindrical objective lens that uses one of the two circumferential areas to receive the annular rays of light as reflected from said circumferential reflecting surface and which allows the light emerging from the other circumferential area to be focused on said surface, said tester detecting the size of a defect on the basis of an output signal from said light receiver.

12. The disk tester according to claim 10, wherein said optical member comprises an annular lens for receiving the annular rays of light as reflected from said circumferential reflecting surface and a doughnut-shaped focusing spherical mirror that receives the annular rays of light emerging from said annular lens and which subjects the received annular rays of light to multiple reflections so that the resulting light is focused on said surface, said tester detecting the size of a defect on the basis of an output signal from said light receiver.

13. A disk testing method by which the surface of a disk to be tested is scanned with light beams and the resulting scattered light from said surface is received by a light receiver to generate signals for defect detection, on the basis of which said disk is tested for any surface defects, comprising the steps of receiving annular rays of light by a hollow optical member, focusing the received annular rays of light as light beams on said surface, receiving said scattered light by an objective lens as it travels toward the hollow portion of said optical member, and receiving said scattered light by said light receiver via said objective lens.

14. The method according to claim 13, wherein the angle of illumination of said surface with said annular rays of light by means of said optical member is set at such a value that the point at which said annular rays of light are focused by said optical member will hardly reach the reverse surface of said disk in spite of its vertical displacements.

* * * * *